US012653724B2

(12) United States Patent
Gualteri et al.

(10) Patent No.: US 12,653,724 B2
(45) Date of Patent: Jun. 16, 2026

(54) METHOD AND APPARATUS FOR PRODUCING FLUFF-FREE ABSORBENT CORES

(71) Applicant: Fameccanica.Data S.p.A., San Giovanni Teatino (IT)

(72) Inventors: Diego Gualteri, San Giovanni Teatino (IT); Alessandro Cipriani, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 488 days.

(21) Appl. No.: 18/041,217

(22) PCT Filed: Aug. 9, 2021

(86) PCT No.: PCT/IB2021/057315
§ 371 (c)(1),
(2) Date: Feb. 10, 2023

(87) PCT Pub. No.: WO2022/034468
PCT Pub. Date: Feb. 17, 2022

(65) Prior Publication Data
US 2023/0301841 A1 Sep. 28, 2023

(30) Foreign Application Priority Data
Aug. 11, 2020 (IT) ......................... 102020000019960

(51) Int. Cl.
*A61F 13/15* (2006.01)
*A61F 13/53* (2006.01)
*D04H 1/732* (2012.01)

(52) U.S. Cl.
CPC .. *A61F 13/15658* (2013.01); *A61F 13/15707* (2013.01); *D04H 1/732* (2013.01);
(Continued)

(58) Field of Classification Search
CPC .......... A61F 13/15577; A61F 13/15617; A61F 13/15626; A61F 13/15634;
(Continued)

(56) References Cited

U.S. PATENT DOCUMENTS

| 4,153,488 A | * | 5/1979 | Wiegand | ................ | D04H 1/732 |
| | | | | | 156/181 |
| 4,640,810 A | * | 2/1987 | Laursen | ................ | D04H 1/732 |
| | | | | | 264/518 |

(Continued)

FOREIGN PATENT DOCUMENTS

| EP | 1253231 A2 | 10/2002 |
| EP | 3153141 A1 | 4/2017 |
| WO | 03073971 A2 | 9/2003 |

OTHER PUBLICATIONS

International Search Report dated Jan. 5, 2022. 12 pages.

*Primary Examiner* — Michael A Tolin
(74) *Attorney, Agent, or Firm* — RMCK Law Group PLC

(57) ABSTRACT
A method and apparatus for producing fluff-free absorbent cores for absorbent sanitary articles, wherein loose unbound fibers and superabsorbent granular material dispersed in the loose unbound fibers are deposited on a movable surface and subsequently the fibers are mixed and bound together in such a way as to form an absorbent structure of bound fibers in which superabsorbent granular material is mixed and incorporated.

4 Claims, 2 Drawing Sheets

(52) U.S. Cl.
CPC .............. *A61F 2013/15861* (2013.01); *A61F 2013/15943* (2013.01); *A61F 2013/530489* (2013.01)

(58) Field of Classification Search
CPC ............ A61F 13/15642; A61F 13/1565; A61F 13/15658; A61F 13/15707; A61F 13/15723; A61F 13/15804; A61F 13/531; A61F 13/539; A61F 2013/15821; A61F 2013/15861; A61F 2013/15878; A61F 2013/15934; A61F 2013/15943; A61F 2013/15975; A61F 2013/15983; A61F 2013/15991; A61F 2013/530131; A61F 2013/530182; A61F 2013/530218; A61F 2013/530226; A61F 2013/530233; A61F 2013/53024; A61F 2013/530379; A61F 2013/530481; A61F 2013/530489; A61F 2013/530591; A61F 2013/5395; A61F 2013/53966; A61F 2013/53975; D04H 1/407; D04H 1/44; D04H 1/45; D04H 1/46; D04H 1/492; D04H 1/498; D04H 1/54; D04H 1/541; D04H 1/5412; D04H 1/5418; D04H 1/542; D04H 1/72; D04H 1/732; D04H 1/736; D04H 1/74; D04H 1/76

See application file for complete search history.

(56) References Cited

U.S. PATENT DOCUMENTS

| | | | |
|---|---|---|---|
| 4,765,780 A | 8/1988 | Angstadt | |
| 6,479,415 B1 | 11/2002 | Erspamer et al. | |
| 2005/0165371 A1* | 7/2005 | Giacometti | D04H 1/4258 |
| | | | 604/367 |
| 2006/0233966 A1* | 10/2006 | Marduel | B29B 15/12 |
| | | | 427/475 |
| 2012/0231691 A1* | 9/2012 | Peyras-Carratte | D04H 1/413 |
| | | | 427/195 |
| 2017/0095379 A1* | 4/2017 | Cipriani | A61F 13/15731 |

* cited by examiner

METHOD AND APPARATUS FOR PRODUCING FLUFF-FREE ABSORBENT CORES

CROSS-REFERENCE TO RELATED APPLICATIONS

This application is a 371 National Stage of International Application No. PCT/IB2021/057315, filed Aug. 9, 2021, which claims priority to Italian Patent Application No. 102020000019960 filed Aug. 11, 2020. The disclosure of each of the above applications is incorporated herein by reference in its entirety.

FIELD OF THE INVENTION

The present invention relates to a method and an apparatus for producing fluff-free absorbent cores.

The invention was developed with a view to its application for producing absorbent sanitary articles such as, for example, diapers and diaper-pants for babies, incontinence pads for adults, sanitary towels for women, and similar articles intended to absorb body fluids.

The method and the apparatus according to the present invention may also be used to produce continuous absorbent sheets, which are subsequently cut or shaped in-line to form discrete absorbent cores.

DESCRIPTION OF THE PRIOR ART

Absorbent sanitary articles typically have a layered structure comprising an outer sheet or backsheet impermeable to liquids, an inner sheet or topsheet permeable to liquids and intended to be placed in contact with the user's skin, and an absorbent core that has the function of capturing and storing body fluids.

The absorbent cores often comprise superabsorbent granular materials. These superabsorbent materials are known by various names such as, for example, SAP (Super Absorbent Polymer) or AGM (Absorbent Gelling Material). In most cases, hydro-gelling materials are used that are capable of absorbing and capturing the liquid.

Most absorbent cores of absorbent sanitary articles currently on the market belong to one of the following two categories:

classic absorbent core formed by defibrated cellulose (also known as cellulose fluff) mixed with superabsorbent granular material;

fluff-free absorbent core formed by one or more non-woven sheets with superabsorbent granular material deposited on the surface or trapped inside the non-woven sheets.

In recent years, fluff-free absorbent cores have undergone major developments, and have gradually been used to replace classic absorbent cores. The evolution of the market towards fluff-free absorbent cores has prompted many manufacturers of absorbent sanitary articles and raw materials to develop sheets of ATB (Air Through Bonding) material, which are more suitable for producing absorbent cores in terms of capacity to trap particles of SAP and in terms of softness to confer softness to the absorbent core in the absence of cellulose fluff. To fulfill these functions, ATB materials must be very bulky and, therefore, the sheets are very thick. This leads to the following problems:

the transport of these materials is not very efficient because the mass/volume ratio is very low;

the duration of the reels in the machine is very low and involves problems related to frequent reel changes;

the tension with which the sheet is managed in the machine may cause a reduction in the characteristic properties of the sheets themselves (reduction in thickness, loss of softness, etc.);

the entrapment of the superabsorbent material inside the ATB material may be difficult since the fibers are bound together.

EP-A-3153141 by the same applicant describes a method for producing a fluff-free absorbent structure for absorbent sanitary articles, wherein superabsorbent granular material is distributed on a non-woven layer with fibers bound by hot air (Air Through Bonding or ATB), and wherein the non-woven layer is volumized by means of a toothed portion that raises and opens the fibers to favor the penetration of the particles of superabsorbent material inside the bound fibers of the non-woven layer. The problem with this solution is that the superabsorbent granular material tends to remain on the surface of the non-woven layer with bound fibers and it is difficult to obtain a uniform mixing of the superabsorbent granular material and the bound fibers.

EP-A-3153141 also discloses an embodiment in which loose unbound fibers are deposited on a movable surface, and the superabsorbent granular material is distributed over the loose unbound fibers. After deposition of the superabsorbent granular material, the loose unbound fibers are opened to facilitate the penetration of the superabsorbent material particles into the fibers. In this embodiment, the fibers remain loose, which entails a poor consistency of the absorbent structure and the risk of dispersion of the superabsorbent granular material during the subsequent processing steps.

U.S. Pat. No. 6,479,415 B1 discloses cores for absorbent sanitary articles formed by unwinding a non-woven sheet from a roll, bound in a manner having a sufficient consistency, which may also contain particles of superabsorbent material (SAP). The consolidation systems used to provide dimensional stability to the sheet include: gluing with latex, welding with thermoplastic fibers or powders, hydroentanglement, needling, carding or the like.

WO 03/073971 A2 describes a method wherein a first sheet consisting at least partially of absorbent fibers is combined with a non-woven support and with an acquisition and distribution layer. Particles of a superabsorbent polymer are inserted into the composite tape formed in this way.

EP 1 253 231 A2 discloses a method for forming a fiber web for use in absorbent products wherein separate air streams containing fibers are fed to different forming wheels. The sheet layers are combined downstream of the forming wheels to form a common fiber sheet. One of the air streams containing fibers may also contain superabsorbent particles.

U.S. Pat. No. 4,765,780 A discloses an apparatus for producing absorbent cores having a plurality of components, wherein at least one of the components contains discrete particles of an absorbent gelling material.

OBJECT AND SUMMARY OF THE INVENTION

The object of the present invention is to provide a method and an apparatus for producing fluff-free absorbent cores that overcome the problems of the prior art.

According to the present invention, this object is achieved by a method and by an apparatus having the characteristics forming the subject of at least claim 1.

The claims form an integral part of the technical disclosure provided in relation to the invention.

The present invention involves introducing a process of deposition of loose, fluff-free unbound fibers in a production line of absorbent sanitary articles, in order to build a fluff-free sheet of unbound fibers in which the particles of superabsorbent granular material are trapped, and subsequently binding the fibers together through thermal (hot air or calender), mechanical (needling), chemical (for example by resins), or other processes.

Loose unbound fibers may be deposited using a 3D Lofting process, a technology developed by the Dilogroup company, which uses high pressure air flows to convey the fibers and deposit them with precision on a movable porous support connected to a suction source.

Alternatively, the loose fibers may be deposited by a carding process.

Producing the absorbent cores directly in the production line of absorbent sanitary articles eliminates the aforesaid problems relating to the in-line use of non-woven sheets with high thickness.

Furthermore, by producing the absorbent cores starting from unbound fibers, the need to provide unwinding devices of raw materials from reels is avoided, and it is possible to obtain different structures bound in the required way without being restricted by the availability of suppliers of raw materials in reels.

Furthermore, the formation of the absorbent cores in-line allows creation of absorbent cores with structures that cannot be made using ATB non-woven sheets or other high loft sheets.

The present invention allows a reduction in the cost of the raw materials of the product because the production steps of the non-woven sheets are shifted in the machine for producing absorbent sanitary articles. This increases the flexibility of producers who can produce products with properties commensurate with project specifications that are currently restricted to the availability of raw materials made available to producers of raw materials.

An additional advantage is that storage costs are significantly reduced and the possibility that stored raw materials may deteriorate before being used.

BRIEF DESCRIPTION OF THE DRAWINGS

The invention will now be described in detail with reference to the attached drawings, given purely by way of non-limiting example, wherein.

DETAILED DESCRIPTION

Figure 1:
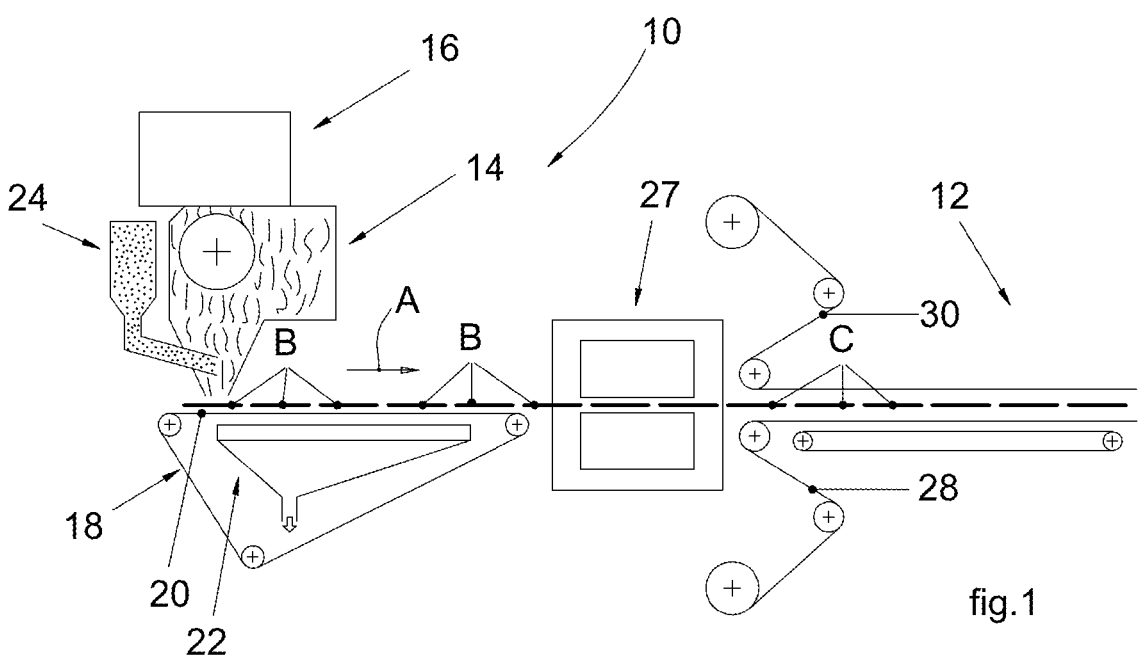
FIG. 1 is a schematic view of a first embodiment of an apparatus for producing absorbent cores C according to the present invention.

With reference to FIG. 1, numeral 10 indicates an apparatus for producing absorbent cores according to the present invention.

The apparatus 10 is arranged in line with respect to an assembly machine 12 configured for producing absorbent sanitary articles. The assembly machine 12 is only represented schematically in the figures, and it is understood that it can be made according to any one of the known architectures in the sector of producing absorbent sanitary articles. The assembly machine 12 may be configured to operate according to the Machine Direction production technique in which the absorbent sanitary articles being formed advance with their prevailing development direction aligned with the machine direction or according to the Cross Machine Direction production technique, in which the absorbent sanitary articles being formed advance with their prevailing development direction transverse with respect to the machine direction. The machine 12 is formed by a set of apparatuses and devices which carry out the assembly of the different components of the absorbent sanitary articles. In particular, the machine 12 may be configured to assemble together: absorbent cores, topsheet and backsheet layers, elasticated waist bands, elastic elements for the legs (leg cuffs), side panels, closure formations, and any other component necessary for producing absorbent sanitary articles, as is well known in the field.

For the purposes of the present invention, the constructional details of the assembly machine 12 are not relevant. What is relevant for the purposes of the present invention is that the apparatus 10 for producing absorbent cores is arranged in line with the assembly machine 12, which carries out the assembly of the absorbent cores with the other components of the absorbent sanitary articles.

The apparatus 10 comprises a fiber deposition unit 14 configured to deposit fluff-free loose unbound fibers coming from a fiber stock 16 onto a movable surface. In a possible embodiment, the deposition of the loose fibers may be carried out with a 3D lofting process developed by the Dilogroup company. The deposition process of fibers called 3D lofting involves generating high pressure air flows that transport the loose fibers and orient them. The high pressure air flows project the loose fibers onto a movable suction surface. The combination of high pressure air jets and the suction to which the target movable surface is subjected allow obtainment of three-dimensional formations of the loose fibers with high precision.

The construction details of a fiber deposition unit 14 operating according to the 3D lofting process are described in detail in documents EP-A-3450603 and EP-A-3450604.

The fibers used in the method according to the present invention are fibers normally used for producing non-woven sheets and may be:

synthetic fibers such as polyester, polyethylene, polypropylene, polyurethane, polyamide, acrylate, cellulose acetate, cupro, lyocell, modal, viscose or rayon, or their mixtures, or natural fibers such as cotton, linen, hemp, jute, ramie, coconut, pineapple, gorse, hibiscus, straw, bamboo, soy, kapok, eucalyptus, or their mixtures.

The fibers used in the method according to the present invention are fibers without cellulose fluff (defibrated cellulose).

The deposition of the loose unbound fibers may be carried out on a movable surface fluidly connected to a suction source. In a possible embodiment, the deposition of the loose unbound fibers may be carried out on a porous conveyor belt 18 having an upper branch 20 facing a suction chamber 22 connected to a source of sub-atmospheric pressure. In possible embodiments, the fiber deposition unit may deposit the fluff-free loose unbound fibers on the outer surface of a forming wheel as in standard processes for forming absorbent cores based on cellulose fluff, as described, for example, in EP-B1-2775975.

The conveyor belt or the forming wheel may be provided with pockets in which the fibers are deposited. These pockets may be shaped to form one or more substantially fiber-free channels in the absorbent core.

The loose unbound fibers may be deposited on a porous substrate, formed, for example, by a non-woven sheet, which advances on a conveyor belt or on the outer surface of a forming wheel, as in traditional processes for producing absorbent cores based on cellulose fluff. Therefore, the process step of the present invention that involves depositing loose, unbound fibers on a movable surface includes both the case wherein the movable surface is the surface of a conveyor belt or of a forming wheel and the case wherein the movable surface is the surface of a movable substrate.

The fiber deposition unit 14 may be configured to deposit the loose unbound fibers onto a movable surface to form an array of blanks of discrete absorbent cores B advancing in the machine direction indicated by the arrow A. The blanks of absorbent cores B may be oriented with their prevailing development direction parallel or transverse to the machine direction A.

The blanks of absorbent cores B may have a rectangular shape or may be shaped according to profiles of various types. The blanks of absorbent cores B may be provided with longitudinal or transverse channels, and may also have a three-dimensional conformation in the Z direction. The blanks of absorbent cores B may be made of fibers of different types (layered, mixed or different colors). The blanks of absorbent cores B may be formed with a variable density layering both in the Z direction and in the direction transverse to the machine direction A.

The apparatus 10 comprises a dispensing device 24 configured to deliver metered quantities of superabsorbent granular material. In the embodiment illustrated in FIG. 1, the dispensing device 24 is arranged to dispense the superabsorbent granular material into the loose, unbound fibers before the fibers are deposited on the movable surface. In this embodiment, the fiber deposition unit 14 deposits loose unbound fibers mixed with superabsorbent granular material on the movable surface. The superabsorbent granular material may be mixed with the loose unbound fibers within a forming chamber or flows of loose unbound fibers and flows of superabsorbent granular material may be formed, which cross each other prior to deposition of the fiber mixture and superabsorbent material. In this way, the blanks of absorbent cores B deposited on the movable surface comprise a mixture of loose unbound fibers and superabsorbent granular material.

The loose unbound fibers to which superabsorbent granular material has been added undergo a binding process in which the fibers are bound together by entrapping superabsorbent granular material between the bound fibers.

The process of binding the fibers, following the process of depositing the fibers and applying superabsorbent granular material, is carried out by passing the blanks of absorbent cores B through a fixing unit 27. The fixing of the fibers may be carried out by means of thermal or mechanical processes of the type used for fixing the fibers of the non-woven sheets. For example, the fixing of the fibers may be carried out by means of flows of hot air that weld the fibers together, according to a process known as air fixing (Air Through Bonding or ATB) or by passing loose unbound fibers added to superabsorbent material between heated calender rollers. The fixing of the fibers may also be carried out by means of needle punching or similar cold mechanical fixing processes which carry out mechanical binding and anchoring of the fibers. By controlling the degree of attachment of the fibers, it is possible to define areas of the cores with variable integrity both in the Z direction and in the transverse direction.

At the outlet of the fixing unit 27, an array of discrete absorbent cores C is obtained having an absorbent body formed by bound fibers and superabsorbent granular material distributed between the bound fibers, wherein the superabsorbent granular material has been dispersed among the fibers before the fixing of the fibers.

The finished absorbent cores C are fed in-line to the assembly machine 12. For example, the finished absorbent cores C at the outlet of the fixing unit 27 may be enclosed between a backsheet layer 28 and a topsheet layer 30 as is customary in the production of absorbent sanitary articles.

Figure 2:
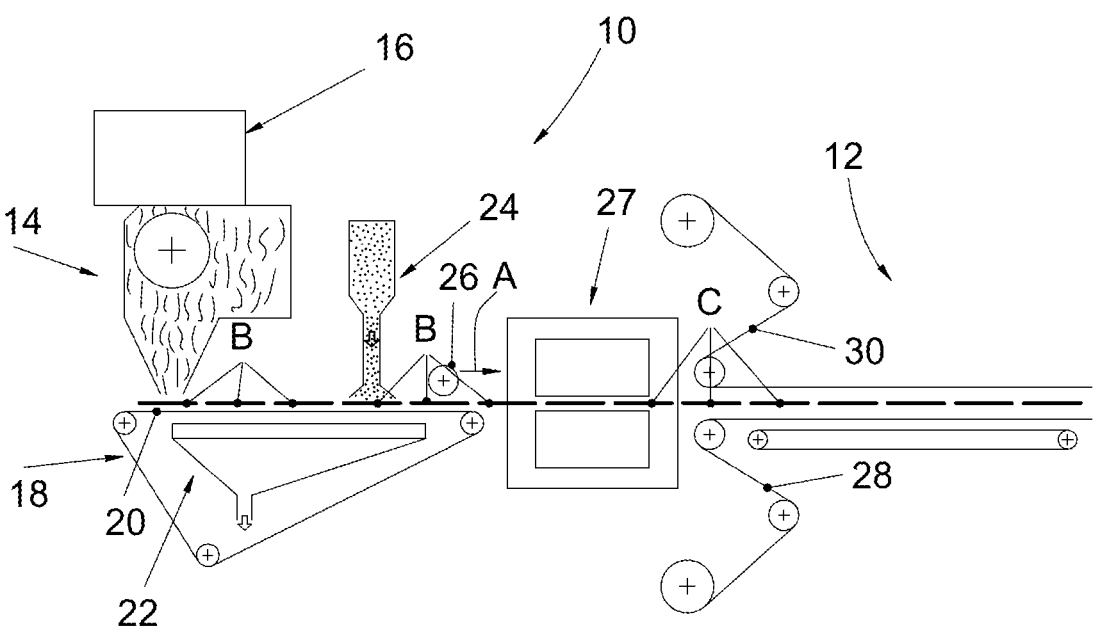
FIGS. 2, 3 and 4 are schematic views illustrating a second, a third and a fourth embodiment of an apparatus for producing absorbent cores according to the present invention.
Figure 3:
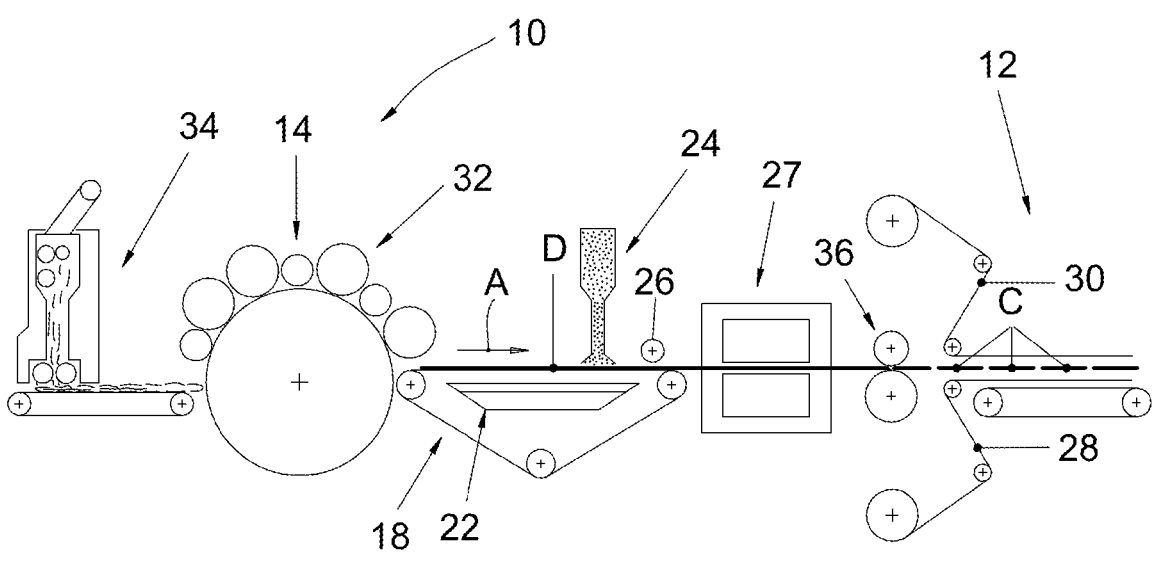
Figure 4:
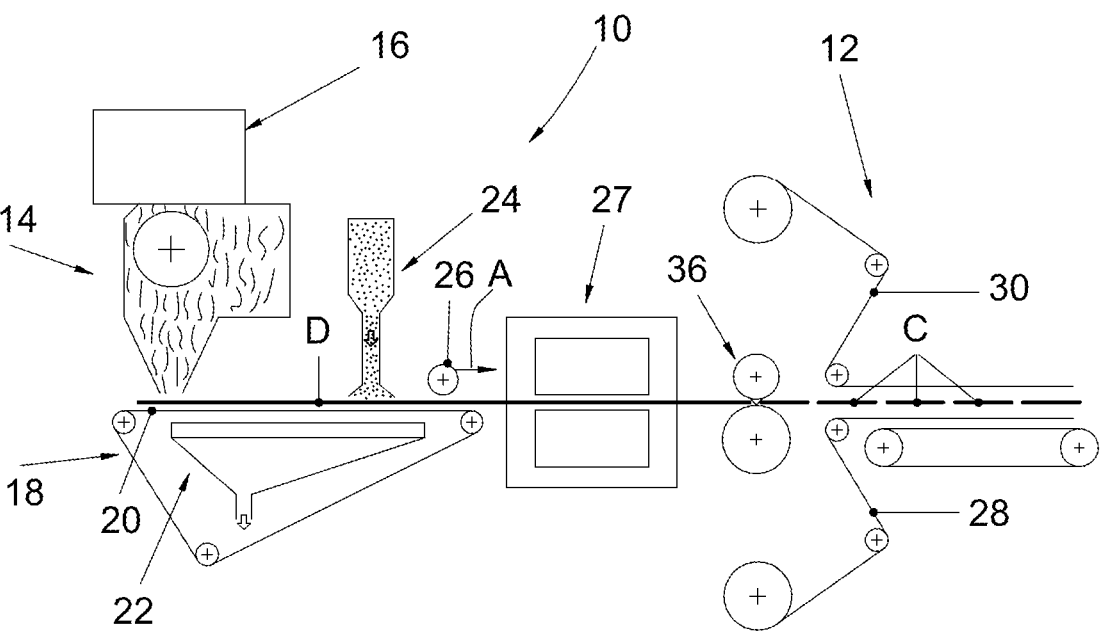

FIGS. 2, 3 and 4 illustrate a second, a third and a fourth embodiment of an apparatus for producing absorbent cores according to the present invention. The elements corresponding to those previously described are indicated with the same numerical references.

In the embodiment illustrated in FIG. 2, the fiber deposition unit 14 forms blanks of absorbent cores B on the movable surface, composed of loose unbound fibers and free from superabsorbent material. A dispensing device 24 is arranged downstream of the fiber deposition unit 14 with reference to the machine direction A, and delivers superabsorbent granular material onto blanks of absorbent cores B. The superabsorbent granular material may be arranged in layers, alternating layers of loose unbound fibers deposited by one or more fiber deposition units 14 with layers of superabsorbent granular material deposited by one or more dispensing devices 24.

The blanks of absorbent cores B on which the superabsorbent granular material has been deposited may be subjected to a mixing step carried out in a mixing unit 26 configured to mix the superabsorbent granular material into the loose unbound fibers. The mixing unit 26 may comprise: rotating brushes, gears, electrostatic devices, air jets, water jets, etc. The mixing unit may also be provided in the embodiment of FIG. 1, even if in this case the superabsorbent granular material has already been mixed with the loose fibers before their deposition.

In the embodiment illustrated in FIG. 3, the fiber deposition unit 14 comprises a card 32 fed by a fiber loader 34. The card 32 produces a continuous web of loose unbound fibers D which is deposited onto a movable surface, for example, on a suction conveyor 18. A dispensing device 24 is arranged to dispense superabsorbent granular material into the loose unbound fibers of the continuous web D as it advances in the machine direction A. Downstream of the dispensing device 24, a mixing unit 26 may be arranged, which favors the distribution of superabsorbent granular material between the loose fibers of the continuous web D. The continuous web of loose unbound fibers D in which the superabsorbent granular material has been distributed is passed through a fixing unit 27 to fix the fibers. At the outlet of the fixing unit 27, a continuous sheet of bound fibers containing superabsorbent granular material distributed between the bound fibers is obtained. The continuous sheet of bound fibers may be cut in a transverse direction by a cutting unit 36 that produces a continuous array of discrete absorbent cores C. The discrete absorbent cores C are supplied in line to an assembly machine 12 as described above.

In the embodiment illustrated in FIG. 4, a fiber deposition unit 14, for example, a 3D lofting fiber deposition unit, deposits a continuous web of loose unbound fibers D. The continuous web of loose unbound fibers D may already have superabsorbent granular material added at the outlet of the fiber deposition unit 14, or the superabsorbent granular material may be applied by a dispensing device 24 located downstream of the fiber deposition unit 14. The 3D lofting fiber deposition technique allows a continuous web D with shaped sides to be formed. The continuous web of loose unbound fibers D with added superabsorbent granular material is passed through a fixing unit 27 to fix the fibers as in the embodiment of FIG. 3. Then, the continuous sheet of bound fibers may be cut in a transverse direction by a cutting unit 36 which produces a continuous array of discrete absorbent cores C. The discrete absorbent cores C are supplied in line to an assembly machine 12 as described above.

The main technical advantage connected to the production of absorbent cores C with the methods described above is the possibility of better incorporating the particles of superabsorbent material between the fibers because the particles of superabsorbent material are incorporated in the loose unbound fibers before the fibers are fixed together.

The absorbent cores thus produced are more intact than a traditional fluff-free product, both in dry and wet conditions.

These methods make it possible to reduce the amount of glue for fixing the superabsorbent material, and make it possible to produce a glue-free absorbent core, defined as an absorbent core containing an amount of glue less than 20% of the total amount of glue applied to the absorbent sanitary article. Under certain conditions, the glue can be completely eliminated.

Of course, without prejudice to the principle of the invention, the details of construction and the embodiments may be varied, with respect to that described, purely by way of non-limiting example, without thereby departing from the scope of the invention as defined by the following claims.

The invention claimed is:

1. An apparatus for producing fluff-free absorbent cores for absorbent sanitary articles, comprising:
   a fiber deposition unit configured to deposit loose unbound fibers onto a movable surface;

a dispensing device configured to apply superabsorbent granular material into said loose unbound fibers,
   a mixing unit configured to mix said loose unbound fibers and the superabsorbent granular material deposited on said movable surface, and
   a fixing unit arranged downstream of said mixing unit and configured to bind said loose unbound fibers together so as to form an absorbent structure of bound fibers in which the superabsorbent granular material is incorporated,
   wherein the fixing unit is configured to carry out binding together said loose unbound fibers by a thermal or mechanical process,
   wherein the movable surface includes a movable suction surface fluidly connected to a suction source, and
   wherein the fiber deposition unit comprises nozzles configured to project the loose unbound fibers onto the movable suction surface fluidly connected to the suction source, by pressurized air jets.

2. The apparatus according to claim 1, wherein the fixing unit binds together said loose unbound fibers by:
   welding the fibers together by Air Through Bonding, or
   passing the loose unbound fibers mixed with the superabsorbent material between heated calender rollers; or
   mechanical binding and anchoring of the loose unbound fibers.

3. The apparatus according to claim 1, wherein said mixing unit comprises a rotating brush, gears, or an electrostatic device.

4. The apparatus according to claim 1, wherein said dispensing device is configured to apply the superabsorbent granular material into said loose unbound fibers after depositing said loose unbound fibers onto said movable surface.

* * * * *